Figure 1:
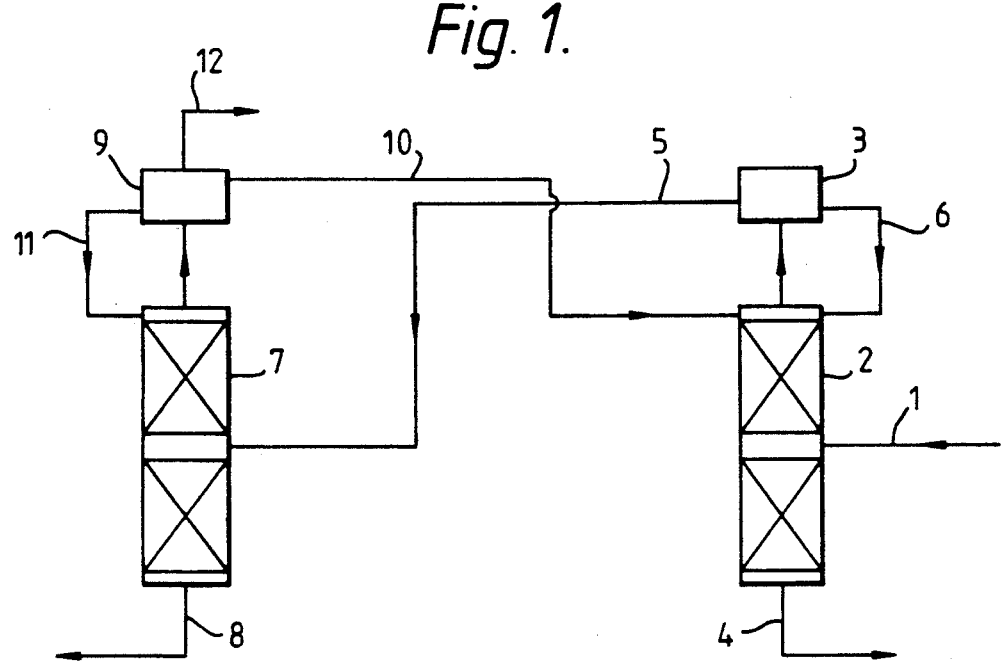

United States Patent [19]
Taylor et al.

[11] Patent Number: 5,211,020
[45] Date of Patent: May 18, 1993

[54] PROCESS FOR SEPARATING HFA 134A

[75] Inventors: Andrew M. Taylor, Huntingdon; Robert W. Wheelhouse, Runcorn, both of England

[73] Assignee: Imperial Chemical Industries, PLC, London, England

[21] Appl. No.: 724,927

[22] Filed: Jul. 2, 1991

[30] Foreign Application Priority Data

Jul. 4, 1990 [GB] United Kingdom ............... 9014851
Jul. 4, 1990 [GB] United Kingdom ............... 9014852

[51] Int. Cl.$^5$ .................................................. F25J 3/00
[52] U.S. Cl. ............................................. 62/11; 62/24; 570/262
[58] Field of Search ............... 62/9, 11, 20, 23, 24; 570/262

[56] References Cited

U.S. PATENT DOCUMENTS 4,373,942  2/1983  Wright ................................ 62/23
4,599,096  7/1986  Burr .................................... 62/20

Primary Examiner—Ronald C. Capossela
Attorney, Agent, or Firm—Cushman, Darby & Cushman

[57] ABSTRACT

A method for separating HFA 134a from an HFA 134a-rich mixture thereof with HF and/or CFC 1122 which comprises feeding the mixture to a distillation column to separate an azeotrope or near-azeotrope of HFA 134a and HF and/or CFC 1122 from a residue comprising substantially pure HFA 134a. Starting from an HF-rich mixture of HFA 134a such as a typical product stream in HFA 134a production, the method includes a first distillation step to separate HF from the initial mixture and produce an azeotrope or near azeotrope of HFA 134a and HF which is an HFA 134a-rich mixture.

10 Claims, 1 Drawing Sheet

PROCESS FOR SEPARATING HFA 134A

This invention relates to a process for separating 1,1,1,2-tetrafluoroethane from a mixture thereof with hydrogen fluoride and/or 1-chloro-2,2-difluoroethylene.

Several methods are known for making 1,1,1,2-tetrafluoroethane (HFA 134a) which is useful for example as a refrigerant, as an aerosol propellant and as a foam blowing agent. In particular, it is known to make HFA 134a by reacting hydrogen fluoride (HF) with various $C_2$ compounds.

At some stage in these processes, a reaction product is formed containing HFA 134a and HF and, usually, other halogenated organics. Not only is it necessary to isolate the HFA 134a in a substantially pure form but it is also essential to the economics of the process to recover the HF and any other unchanged starting materials for recycling to the fluorination reactor. One method that has been proposed for separating R134a and HF is to scrub the mixed gases with water.

In some at least of the known processes a by-product of the reaction is 1-chloro-2,2-difluoroethylene (CFC 1122). This by-product is toxic and needs to be removed from HFA 134a or at least reduced to an extremely low level, e.g. below 10 ppm and preferably lower. Several methods have been proposed for removing CFC 1122 from HFA 134a, including (i) permanganate treatment, (ii) reaction with HF over chromia and (iii) absorption using a molecular sieve such as a zeolite or a carbon molecular sieve.

It has now been found that azeotropic mixtures of HFA R134a with HF and/or CFC 1122 are formed at various temperatures and pressures and it has further been found that azeotropic distillation of HFA 134a/HF and/or CFC 1122 mixtures, as hereinafter described, provides a highly efficient and economic method of separating the materials, especially for removing essentially pure HFA 134a from the mixtures.

According to the present invention there is provided a method for the separation of 1,1,1,2-tetrafluoroethane (HFA 134a) from a HFA 134a-rich mixture thereof with HF and/or CFC 1122 which comprises passing said mixture through a distillation column whereby to separate an azeotrope or near-azeotrope of HFA 134a and HF and/or CFC 1122 from a residue comprising essentially pure HFA 134a and collecting said residue from the distillation column.

It has been found that azeotropic mixtures of HFA 134a and HF are formed at various temperatures and pressures:

| Pressure (bars absolute) | Temperature (°C.) | HFA 134a (mole fraction) | HF (mole fraction) |
| --- | --- | --- | --- |
| 0.5 | −42 | 0.73 | 0.27 |
| 1.0 | −27 | 0.76 | 0.24 |
| 3.0 | 0 | 0.82 | 0.18 |
| 6.0 | 20 | 0.85 | 0.15 |
| 10.0 | 38 | 0.87 | 0.13 |
| 16.0 | 56 | 0.87 | 0.13 |

It has also been found that azeotropic mixtures of HFA 134a and CFC 1122 are formed at various temperatures and pressures:

| Pressure (bars absolute) | Temperature (°C.) | HFA 134a (mole fraction) | HF (mole fraction) |
| --- | --- | --- | --- |
| 0.5 | −44 | 0.74 | 0.26 |
| 1.0 | −29 | 0.77 | 0.23 |
| 3.0 | −2 | 0.82 | 0.18 |
| 6.0 | 18 | 0.86 | 0.14 |
| 10.0 | 36 | 0.89 | 0.11 |
| 16.0 | 55 | 0.92 | 0.08 |

It has also been found that ternary azeotrope of HFA 134a, HF and CFC 1122 are formed at the various temperatures and pressures given in the above tables.

By the term "near-azeotropic mixture" there is meant a mixture which contains the components thereof in amounts close to but not exactly equal to the amounts in the actual azeotropic mixture.

The invention utilizes these azeotrope-forming capabilities of the components of mixtures to effect a separation of essentially-pure HFA 134a from the mixtures. Thus passing to a distillation column operating at a temperature T° C. (and associated pressure P) a mixture of HFA 134a with HF and/or CFC 1122 containing a proportion of HFA 134a greater than the azeotrope between HFA 134a and the other component(s) at T° C. and pressure P, results in removal of the azeotrope or a near-azeotrope from the top of the column and a liquid residue comprising essentially pure HFA 134a.

Accordingly by the term "HFA 134a-rich mixture" as used herein there is meant a mixture of HFA 134a with HF and/or CFC 1122 which contains a proportion of HFA 134a greater than the azeotrope between HFA 134a and the other component(s) at the particular temperature and associated pressure at which the distillation column is operated.

By way of example and having regard to the tables above, the term "HFA 134a-rich mixture" means in relation to operation at 38° C. (and 10 bar) or 56° C. (and 16 bar) a mixture of HFA 134a and HF containing a mole fraction HFA 134a greater than 0.87, whilst in relation to operation at −42° C. (and 0.5 bar), the term means a mixture containing a mole fraction HFA 134a greater than 0.73. It is to be understood that the precise figures quoted above and in the tables above are approximate only and are not to be interpreted as imposing a precise numeral restriction on the scope of the term "HFA 134a-rich mixture" or the invention.

It will be readily apparent, that for any particular HFA 134a-rich mixture, lowering the temperature of operation of the distillation column reduces the amount of HFA 134a removed by the column as an azeotrope or near-azeotrope and hence increases the amount of essentially pure HFA 134a separated from the mixture. However, whilst there may be an advantage from operating at very low temperature and below 1 bar pressure in terms of HFA 134a separated, in practice it is convenient to operate the separation at about atmospheric pressure and about −27° C.

As stated, the invention resides in recovering HFA 134a from a HFA 134a-rich mixture of HFA 134a with HF and/or CFC 1122. In practice, however, the product stream from a HFA 134a production unit will often be HF-rich rather than HFA 134a-rich and in fact typically will contain a major proportion of HF. Such a product stream will require treatment to produce a HFA 134a-rich mixture prior to use in the invention. Any method for reducing the HF content of the mixture and creating a HFA 134a-rich mixture may be employed but we have found that an azeotropic distillation technique is particularly suitable.

In this technique, distillation of the HF-rich mixture results in removal of an azeotrope or near azeotrope of HFA 134a and HF and a residue comprising liquid HF. The resulting azeotrope or near-azeotrope may be employed as the 134a-rich mixture in the present invention; thus with reference to the tables above (c), distillation of the HF-rich mixture at high temperature (and high pressure) can result in an azeotropic or near-azeotropic mixture containing a mole fraction 134a of about 0.87; distillation of this azeotropic or near azeotropic mixture at a lower temperature (and lower pressure) can result in the formation of another azeotrope or near-azeotrope containing a mole fraction HFA 134a of about 0.73 with associated separation of essentially pure (liquid) HFA 134a.

In practice, the HFA 134a product stream from a production unit is likely to contain only a small amount of CFC 1122, for example about 20 ppm, and even during the HFA 134a work up procedure there is unlikely to be produced a HFA 134a/CFC 1122 mixture which is not a HFA 134a-rich mixture. Such HFA 134a-rich mixtures do not require a pre-treatment before use in the invention. However, in the event that a CFC 1122-rich mixture were to be treated it can be distilled in a preliminary distillation column as described above in respect of HF-rich mixtures. Since the treatment of a CFC 1122-rich mixture has little practical significance, the invention is described hereinafter only in respect of an HF-rich mixture.

According to a preferred embodiment of the invention there is provided a method for the separation of 1,1,1,2-tetrafluoroethane (HFA 134a) from an initial mixture thereof with HF, said method comprising passing the mixture through a first distillation column whereby to separate a first azeotrope or near azeotrope of HF and HFA 134a from a first still residue comprising HF, feeding the azeotrope or near-azeotrope to a second distillation column maintained at a lower pressure than the first distillation column whereby to separate a mixture comprising a second azeotrope or near-azeotrope of HF and HFA 134a from a second still residue comprising 134a.

In the case of an initial mixture comprising a major proportion of HF and a minor proportion of HFA 134a, the preferred method of the invention separates both HF and HFA 134a and comprises:

(1) passing the initial mixture through a first distillation column whereby to separate HF from a relatively low boiling azeotropic or near-azeotropic mixture comprising a major proportion of HFA 134a and a minor proportion of HF;
(2) recovering HF from the bottom of the column;
(3) removing the azeotropic or near azeotropic mixture from the top of the column and feeding it to a second distillation column maintained at a lower pressure than the first column whereby to separate HFA 134a from a relatively low boiling mixture comprising an azeotrope or near-azeotrpic containing a major proportion of HFA 134a and a minor proportion of HF;
(4) removing the relatively low boiling mixture from the top of the second distillation column and returning it to the first distillation column, and
(5) recovering substantially pure HFA 134a from the bottom of the second distillation column.

Included within the invention is a modification of the two-column process decribed hereinbefore wherein a liquid/liquid separation zone is provided between the first and second distillation columns whereby to separate an upper layer rich in HF from a lower layer rich in HFA 134a, as hereinafter described.

According to a further feacture of the invention there is provided a method for the separation of 1,1,1,2-tetrafluoroethane (HFA 134a) from an HF-rich mixture thereof which comprises passing the mixture through a first distillation column whereby to separate a first azeotrope or near-azeotrope of HF and HFA 134a from a first still residue comprising HF, feeding the azeotrope or near-azeotrope to a liquid-liquid separation zone whereby to separate an upper HF-rich layer from a lower HFA 134a-rich layer and pasing said lower layer to a second distillation column whereby to separate a second azeotrope or near-azeotrope of HF and HFA 134a from a second still residue comprising HFA 134a.

Thus, in the case of an initial mixture comprising a major proportion of HF and a minor proportion of HFA 134a, this feature of the invention comprises:

(1) passing the initial HF-rich mixture through a first distillation column whereby to separate HF from a relatively low boiling azeotropic or near-azeotropic mixture comprising a major proportion of HFA 134a and a minor proportion of HF;
(2) recovering HF from the bottom of the column;
(3) removing the mixture from the top of the column and feeding it to a separation zone whereby to separate an upper HF-rich layer from a lower HFA 134a-rich layer;
(4) removing the HFA 134a-rich layer from the separation zone and feeding it to a second distillation column whereby to separate HFA 134a from a relatively low boiling azeotropic or near-azeotropic mixture comprising containing a major proportion of HFA 134a and a minor proportion of HF,
(5) removing the relatively low boiling mixture from the top of the second distillation column and returning it to the separation zone, and
(6) recovering substantially pure HFA 134a from the bottom of the second distillation column.

The HF recovered from the bottom of the first distillation column can be recycled to the fluorination reactor.

Mixtures of HFA 134a and HF form two phases at various temperatures as indicated below:

| Temperature (°C.) | Mole Fraction Upper layer | R134a Lower layer |
|---|---|---|
| −40 | 0.30 ± 04 | 0.92 ± 0.01 |
| −30 | 0.31 ± 04 | 0.92 ± 0.01 |
| −20 | 0.33 ± 04 | 0.92 ± 0.01 |
| −10 | 0.36 ± 04 | 0.92 ± 0.01 |
| 0 | 0.40 ± 04 | 0.92 ± 0.01 |
| 10 | 0.45 ± 04 | 0.92 ± 0.01 |
| 20 | 0.52 ± 04 | 0.92 ± 0.01 |
| 30 | 0.60 ± 04 | 0.92 ± 0.01 |

The critical solution temperature occurs between 30° and 40° C.

Thus, over a range of temperatures, a mixture of HFA 134a and HF separates into an upper layer rich in HF and a lower layer rich in HFA 134a.

The upper layer formed in the separation zone can be returned to the first distillation column whilst the lower layer is passed to the second distillation column which is generally maintained at a pressure from about 0.5 to about 36 bars absolute. The operating pressure is preferably lower than that of the first column where HF is the major component of the initial mixture. The second column separates substantially pure HFA 134a from a mixture comprising an azeotrope or near-azeotrope less rich in HFA 134a than the distillate from the first column. The distillate from the second column can be recycled to the separation zone.

The initial mixture used in the method of the invention may be any HFA 134a-rich mixture of HFA 134a and HF requiring separation. A feature of the method is applicable to HF-rich mixtures obtained in processes for the manufacture of HFA 134a by the reaction of HF with $C_2$ compounds. The mixtures produced in such processes generally contain HF, HFA 134a and other halogenated products such as 2-chloro-1,1,1-trifluoroethane, 2-chloro-1,1,1,2-tetra- fluoroethane and/or trichloroethylene. If necessary, these reaction streams may be given a pre-treatment in order to effect partial or complete removal of one or more of these other constituents.

When treating a mixture wherein HF is the major component, the first distillation column is generally maintained at a pressure from about 0.5 to about 36 bars absolute and separates the bulk of the HF and any other materials heavier than the HFA 134a/HF azetrope from an azeotrope or near-azeotrope rich in HFA 134a, the precise composition depending upon the temperature and pressure of the column. The HF recovered from the bottom of the column can be recycled to the fluorination reactor.

The second distillation column is then generally maintained at a pressure from about 0.4 to about 8 bar absolute, a feature being that the operating pressure in the second column is lower than that of the first column, and separates substantially pure HFA 134a from a mixture comprising an azeotrope or near-azeotrope less rich in HFA 134a than the distillate from the first column. The distillate from the second column can then be recycled to the first column.

The conditions recited for the second column may be adopted where the initial mixture is HFA 134a-rich in respect of HF and/or CFC 1122 and therefor requires only a single distillation column.

Figure 2:
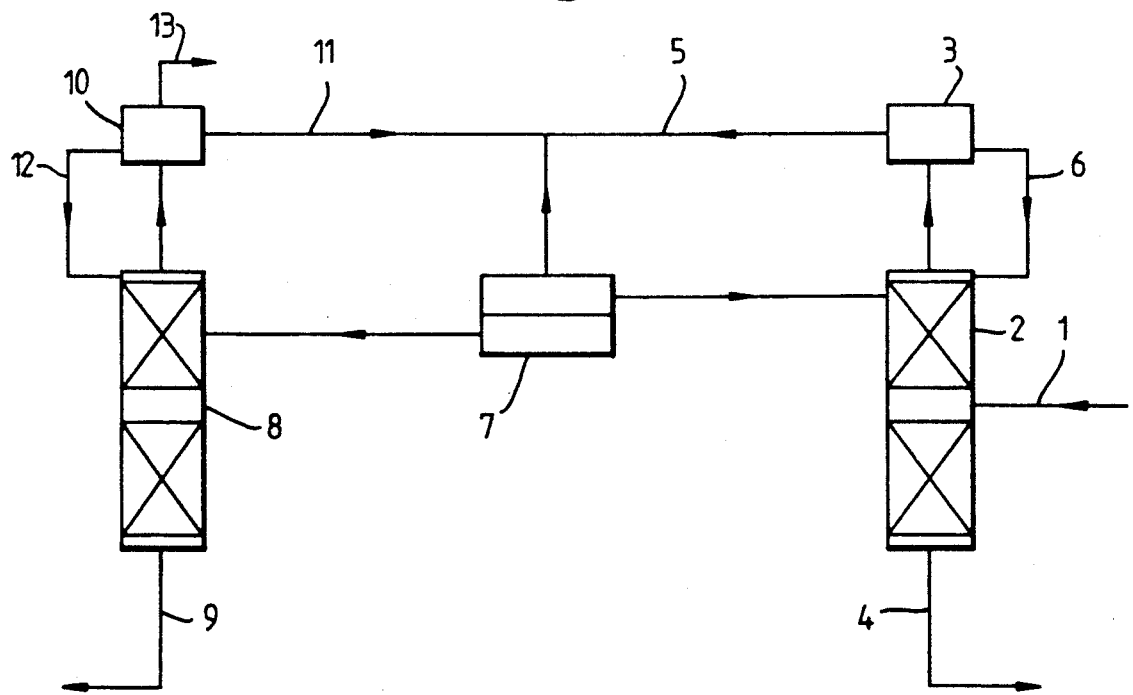

The invention will now be illustrated with reference to the accompanying drawings, FIGS. 1 and 2 being schematic representations of equipment for use in treating a HF-rich mixture of HFA 134a and HF.

A. Referring to FIG. 1, a feed mixture comprising about 20% of HFA 134a and 80% of HF, on a molar basis, is fed via line 1 to a distillation column 2 maintained at a pressure of 16 bars absolute. An azeotrope or near-azeotrope of HFA 134a (87% molar) and HF (13% molar) is taken from the top of the column and condensed in a condenser 3 whilst the residue comprising HF (and various halogenated organics) leaves the column via line 4 for recycling to the fluorination reactor. Part of the condensate from the condenser 3 is fed via line 5 to a second distillation column 7 maintained at a pressure of 3 bars absolute, a reflux flow line 6 leading back to the column 2 from condenser 3. Substantially pure HFA 134a is taken from the bottom of the column 7 via line 8 whilst an azeotrope or near-azeotrope of HFA 134a (82% molar) and HF (18% molar) is taken from the top of the column 7, condensed in condenser 9 and returned via line 10 to the first column 2. A reflux flow line 11 leads from the condenser 9 back to the column 7 and a lights recycle flow line 12 leads from the condenser 9 back to the fluorination reactor.

B. Referring again to FIG. 1, a feed mixture comprising about 6% of R134a, 23% of R133a and 71% of HF on a molar basis, is fed at 75° C. via line 1 to a distillation column 2 maintained at a pressure of 16 bars absolute. An azeotrope or near-azeotrope of R134a (87% molar) and HF (13% molar) is taken from the top of the column and condensed in a condenser 3 whilst the residues comprising HF and R133a leave the column via line 4 for recycling to the fluorination reactor. Part of the condensate from the condenser 3 is fed via line 5 at about 56° C. to a second distillation column 7 maintained at a pressure of 1 bar absolute, a reflux flow line 6 leading back to the column 2 from condenser 3. Substantially pure R134a is taken from the bottom of the column 7 via line 8 whilst an azeotrope or near-azeotrope of R134a (82% molar) and HF (18% molar) is taken from the top of the column 7, condensed in condenser 9, and returned via line 10 at about −29° C. to the first column 2. A reflux flow line 11 leads from the condenser 9 back to the column 7 and a lights recycle flow line 12 leads from the condenser 9 back to the fluorination reactor.

C. This embodiment describes the treatment of a mixture containing the impurity 1122. Referring again to FIG. 1, a feed mixture comprising about 6% of R134a, 23% of R133a, 71% of HF and 0.001% of 1122 on a molar basis, is fed at 75° C. via line 1 to a distillation column 2 maintained at a pressure of 16 bars absolute. An azeotrope or near-azeotrope of R134a (87% molar) and HF (13% molar) containing 1122 (0.1% molar) is taken from the top of the column and condensed in a condenser whilst the residues comprising HF and various halogenated organics leave the column via line 4 for recycling to the fluorination reactor. The residues contain less than $1 \times 10^{-6}$ ppm of 1122. Part of the condensate from the condenser 3 is fed via line 5 at about 56° C. to a second distillation column 7 maintained at a pressure of 1 bar absolute, a reflux flow line 6 leading back to the column 2 from condenser 3. Substantially pure R134a (containing less than $1 \times 10^{-6}$ ppm of 1122) is taken from the bottom of the column 7 via line 8 whilst an azeotrope or near-azeotrope of R134a (82% molar) and HF (18% molar) is taken from the top of the column 7, condensed in condenser 9, and returned via line 10 at about −29° C. to the first column 2. A reflux flow line 11 leads from the condenser 9 back to the column 7 and a lights recycle flow line 12 leads from the condenser 9 back to the fluorination reactor.

During operation of the system, the 1122 content of the vapour mixture fed to condenser 3 from the top of column 2 increases and from time to time this vapour mixture is vented from the system and returned to a suitable point in the 134a production/work-up.

D. Referring to FIG. 2, a feed mixture comprising about 20% of HFA 134a and 80% of HF, on a molar basis, is fed via line 1 to a distillation column 2 maintained at a pressure of 16 bars absolute. An azeotrope of R134a (87% molar) and HF (13% molar) is taken from the top of the column and condensed in a condenser 3 whilst the residues comprising HF and various halogenated organics leave the column via line 4 for recycling to the fluorination reactor. Part of the condensate from the condenser 3 is fed via line 5 to a separation zone 7 maintained at a temperature of 0° C. a reflux flow line 6 leading back to the column 2 from condenser 3. In the separation zone 7, an organic phase comprising 92 mole percent R134a and 8 mole percent HF forms as the bottom layer and an acid phase comprising 60 mole percent HF and 40 mole percent R134a as the top layer. The acid phase is returned from the top of the separation zone 7 to the column 2 whilst the organic phase is fed from the bottom of the separation zone 7 to a second distillation column 8 maintained at a pressure of 3 bars absolute. Substantially pure R134a is taken from the bottom of the column 8 via line 9 whilst an azeotrope of R134a (82% molar) and HF (18% molar) is taken from the top of the column 8, condensed in condenser 10, and returned via line 11 to the separation zone 7. A reflux flow line 12 leads from the condenser 10 back to the column 8 and a lights recycle flow line 13 leads from the condenser 10 back to the fluorination reactor.

E. Referring again to FIG. 2, a feed mixture comprising about 6% of R134a, 23% of R133a and 71% of HF on a molar basis, is fed at 75° C. via line 1 to a distillation column 2 maintained at a pressure of 16 bars absolute. An azeotrope or near-azeotrope of R134a (87% molar) and HF (13% molar) is taken from the top of the column and condensed in a condenser 3 whilst the residues comprising HF and R133a leave the column via line 4 for recycling to the fluorination reactor. Part of the condensate from the condenser 3 is fed at about 56° C. via line 5 to a separation zone 7 a reflux flow line 6 leading back to the column 2 from condenser 3. In the separation zone 7, an organic phase comprising about 92 mole percent R134a and 8 mole percent HF forms as the bottom layer and an acid phase comprising about 60 mole percent HF and 40 mole percent R134a as the top layer. The acid phase is returned from the top of the separation zone 7 to the column 2 (at about −40° C.) whilst the organic phase is fed from the bottom of the separation zone 7 (at about −40° C.) to a second distillation column 8 maintained at a pressure of 1 bar absolute. Substantially pure R134a is taken from the bottom of the column 8 via line 9 whilst an azeotrope or near-azeotrope of R134a (82% molar) and HF (18% molar) is taken from the top of the column 8, condensed in condenser 10, and returned via line 11 at about −27° C. to the separation zone 7. A reflux flow line 12 leads from the condenser 10 back to the column 8 and a lights recycle flow line 13 leads from the condenser 10 back to the fluorination reactor.

We claim:

1. A method for the separation of 1,1,1,2-tetrafluoroethane (HFA 134a) from a HFA 134a-rich mixture thereof with at least one member of the group consisting of HF and 1-chloro-2,2-difluoroethylene (CFC 1122) which comprises passing said mixture through a distillation column and thereby separating an azeotrope or near-azeotrope of HFA 134a and said member from a residue comprising essentially pure HFA 134a and collecting said residue from the distillation column.

2. A method as claimed in claim 1 wherein the HFA 134a-rich mixture is a mixture of HFA 134a and HF derived by distillation from an initial mixture which is HF-rich.

3. A method as claimed in claim 2 which comprises passing the initial mixture which is HF-rich through a first distillation column whereby to separate a first azeotrope or near azeotrope of HF and HFA 134a which is HFA 134a-rich from a first still residue comprising HF, feeding the first azeotrope or near azeotrope thus obtained to a second distillation column maintained at a lower temperature and pressure than the first distillation column and separating in said second distillation column a mixture comprising a second azeotrope or near-azeotrope of HF and HFA 134a from a second still residue comprising HFA 134a.

4. A method as claimed in claim 2 or claim 3 wherein the initial mixture contains a major proportion of HF and a minor proportion of HFA 134a and said method comprises
   (1) passing the initial mixture through a first distillation column and thereby separating HF from a relatively low boiling azeotropic or near azeotropic mixture comprising a major proportion of HFA 134a and a minor proportion of HF,
   (2) recovering HF from the bottom of the first distillation column,
   (3) feeding the azeotropic or near azeotropic mixture from the first distillation column to a second distillation column maintained at a lower temperature and pressure than the first column and thereby separating HFA 134a from a relatively low boiling mixture removed from the top of the second distillation column, said low boiling mixture comprising an azeotrope or near-azeotrope containing a major proportion of HFA 134a and a minor proportion of HF,
   (4) returning the relatively low boiling mixture removed from the top of the second distillation column to the first distillation column, and
   (5) recovering substantially pure HFA 134a from the bottom of the second distillation column.

5. A method as claimed in claim 2 or claim 3 which comprises passing the initial mixture through a first distillation column whereby to separate a first azeotrope or near-azeotrope of HF and HFA 134a from a first still residue comprising HF, feeding the azeotrope or near azeotrope from said first distillation column to a liquid/liquid separation zone whereby to separate an upper HF-rich layer from a lower HFA 134a-rich layer and passing said lower layer to a second distillation column whereby to separate a second azeotrope or near-azeotrope of HF and HFA 134a from a second still residue comprising HFA 134a.

6. A method as claimed in claim 2 or claim 3 which comprises:
   (1) passing the initial HF-rich mixture through a first distillation column whereby to separate HF from a relatively low boiling azeotropic or near-azeotropic mixture comprising a major proportion of HFA 134a and a minor proportion of HF,
   (2) recovering the separated HF from the bottom of the column,
   (3) feeding the azeotropic or near-azeotropic mixture from the top of the first distillation column to a separation zone whereby to separate an upper HF-rich layer from a lower HFA 134a-rich layer,
   (4) feeding said lower HFA 134a-rich layer to a second distillation column whereby to separate HFA 134a from a relatively low boiling azeotropic mixture comprising a major proportion of HFA 134a and a minor proportion of HF,
   (5) returning the low boiling mixture from the top of the second distillation column to the separation zone, and
   (6) recovering substantially pure HFA 134a from the bottom of the second distillation column.

7. A method as claimed in claim 6 wherein the upper HF-rich layer is fed from the separation zone (step 3) to the first distillation column.

8. A method as claimed in claim 7 wherein the second distillation column is operated at a lower temperature and pressure than the first distillation column.

9. A method as claimed in claim 1 wherein the distillation column is operated at a pressure of from 0.5 bar to 36 bars absolute.

10. A method as claimed in claim 9 using two distillation columns and wherein the second distillation column is operated at a pressure of from 0.4 bar to 8 bars absolute.

* * * * *